United States Patent [19]

McCully

[11] 4,383,994

[45] May 17, 1983

[54] HOMOCYSTEINE THIOLACTONE SALTS AND USE THEREOF AS ANTI-NEOPLASTIC AGENTS

[76] Inventor: Kilmer S. McCully, 15 Wildwood St., Winchester, Mass. 01890

[21] Appl. No.: 340,712

[22] Filed: Jan. 19, 1982

[51] Int. Cl.³ .................... A61K 31/38; C07D 333/30
[52] U.S. Cl. ............................... 424/245; 260/330.3; 424/275; 549/3; 549/63
[58] Field of Search ................. 260/330.3; 549/3, 63; 424/245, 275

[56] References Cited

U.S. PATENT DOCUMENTS 4,255,443  3/1981  McCully ............................ 424/275
4,269,849  5/1981  Chan ................................. 424/275

Primary Examiner—Richard Raymond

[57] ABSTRACT

N-Maleyl homocysteine thiolactone amide, N-maleamide homocysteine thiolactone amide, oxalyl homocysteine thiolactone hydroperchlorate, and rhodium trichloride oxalyl homocysteine thiolactone hydroperchlorate are useful as anti-neoplastic agents.

9 Claims, No Drawings

HOMOCYSTEINE THIOLACTONE SALTS AND USE THEREOF AS ANTI-NEOPLASTIC AGENTS

BACKGROUND OF THE INVENTION

1. Field of the Invention

This invention relates to novel derivatives of homocysteine thiolactone, which have anti-neoplastic activity.

2. Prior Art

McCully (U.S. Pat. No. 4,255,443) has proposed that homocysteine thiolactone hydroperchlorate promotes the growth of malignant tumors in laboratory animals. The compound is accordingly useful in laboratory studies on growth of malignant neoplasms, particularly in the evaluation of anti-neoplastic agents.

Other literature references on the metabolism or pharmacology of homocysteine thiolactone derivatives are:

Kilmer S. McCully, "Homocysteine Metabolism in Scurvy, Growth and Arteriosclerosis," *Nature*, 231:391–392 (June 11, 1971).

Kilmer S. McCully, "Homocysteinemia and Arteriosclerosis," *American Heart Journal*, 83:571–573 (April, 1972).

Eliot Spindel and Kilmer S. McCully, "Conversion of Methionine to Homocysteine Thiolactone in Liver," *Biochimica et Biophysica Acta*, 343:687–691 (1974).

Kilmer S. McCully and Robert B. Wilson, "Homocysteine Theory of Arteriosclerosis," *Atherosclerosis*, 22:215–227 (1975).

Kilmer S. McCully and Peter Clopath, "Homocysteine Compounds Which Influence the Growth of a Malignant Neoplasm," *Chemotherapy*, 23:44–49 (1977).

Kilmer S. McCully, "Homocysteine Thiolactone Metabolism in Malignant Cells," *Cancer Research*, 36:3198–3202 (1976).

Chan has proposed, in U.S. Pat. No. 4,269,849, to use gamma-butyrothiolactone amide derivatives for fungicidal purposes.

DESCRIPTION OF THE INVENTION

This invention relates to the following homocysteine thiolactone derivatives:

(a) N-maleyl homocysteine thiolactone amide
(b) N-maleamide homocysteine thiolactone amide
(c) oxalyl homocysteine thiolactone hydroperchlorate
(d) rhodium trichloride oxalyl homocysteine thiolactone hydroperchlorate.

In another aspect, this invention relates to the use of any of the foregoing compounds in a method for decreasing the growth of a malignant neoplasm, comprising administering to an animal afflicted with the neoplasm an amount of one of the foregoing, in admixture with a pharmaceutically acceptable carrier, effective to decrease growth of the neoplasm.

Homocysteine is HSCH$_2$CH$_2$CH(NH$_2$)COOH and the thiolactone is

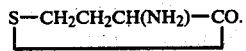

The hydroperchlorate, which is the starting material for making the compounds of this invention, is prepared from the corresponding hydrochloride.

Homocysteine thiolactone hydrochloride is described in DP No. 1,081,466 (1958). Additionally, British Pat. No. 903,322 and Canadian Pat. No. 611,437 relate to the homocysteine thiolactone hydrohalide. British Pat. No. 903,322 notes the compound at column 2, first page, and Canadian Pat. No. 611,437 describes the chlorohydride at column 2, line 62.

Homocysteine thiolactone perchlorate is produced by the following reaction:

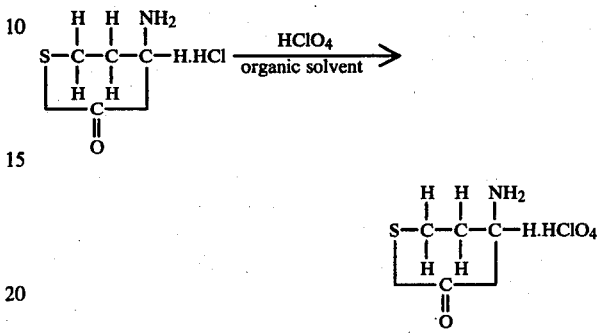

A surprising feature of the foregoing process is that perchloric acid, which is a powerful oxidizing agent, doe not oxidize the sulfur atom of the starting thiolactone to a corresponding sulfinic acid.

The reaction represented by the above equation is carried out in an organic solvent, of which a mixture of chloroform and methanol (4:1 by volume) is preferred.

Selection of the solvent system for the reaction was influenced by the facts that homocysteine thiolactone hydrochloride salt and perchlorate salt have different water solubilities and that the perchlorate, unlike previously reported salts, is soluble in organic solvents. It was found that a solvent system selective with respect to the unlike solubility properties of the hydrochloride and hydroperchlorate should be used. The solvent should include a halogenated hydrocarbon solvent such as chloroform, carbon tetrachloride, or ethylene dichloride as a major component, modified with a minor amount of a lower alkanol (C$_1$–C$_6$), such as methanol, ethanol, isopropanol, etc. Less preferred alternatives for the lower alkanol are dioxane, acetonitrile, or aprotic solvents such as dimethyl formamide (DMF) or dimethyl sulfoxide (DMSO).

A convenient list of industrial solvents for alcohols and chlorinated hydrocarbons is set out in Kirk-Othmer, *The Encyclopedia of Chemical Technology*, 2d ed., 18:565, 1969, at Table 1.

A particularly preferred combination for purposes of this invention is a combination of chloroform and methanol, optimally in a ratio of 4:1 (by volume).

The temperature at which the reaction is performed can be varied over rather wide limits, ranging from a preferred range of 0°–85° C. to a limiting lower range which is solvent dependent and a limiting upper range, depending on the melting point of the crystals produced (about 186° C.).

The reaction is favorably affected by an excess of perchloric acid. The optimal stoichiometry is two moles of perchloric acid per mold of hydrochloride salt reactant. The product perchlorate salt is recovered preferably by concentration on a rotary evaporator to crystallize the salt, which is recrystallized from chloroform and methanol (4:1 by volume) to produce translucent white crystals melting sharply at 186° C.

Unlike other salts, the perchlorate salt is soluble in organic solvents. There appears to be a significant correlation between solubility in organic solvents and in vivo behavior of homocysteine thiolactone derivatives. For example, it has been found that the perchlorate affects the growth of malignant tumors in mice, whereas the hydrochloride is without effect. This indicates that the biological activity of the perchorate is dependent upon its solubility in non-polar solvents. Thus, the solubility of the perchlorate salt in non-polar solvents makes it uniquely useful in many functions and also screens out any possible use by such salts as the hydrohalide.

The unique solubility properties of homocysteine thiolactone perchlorate are also used to advantage in synthesizing novel derivatives of homocysteine thiolactone. N-Maleyl homocysteine thiolactone amide and N-maleamide homocysteine thiolactone amide can conveniently be synthesized in toluene from homocysteine thiolactone perchlorate. Since homocysteine thiolactone hydrochloride is insoluble in organic solvents used for maleylation, a fusion process, which results in racemization to N-fumaryl homocysteine thiolactone amide and a mixture of other products, would have to be used if the hydrochloride were the starting material.

The synthesis of N-maleyl homocysteine lactone amide can be represented by the equation:

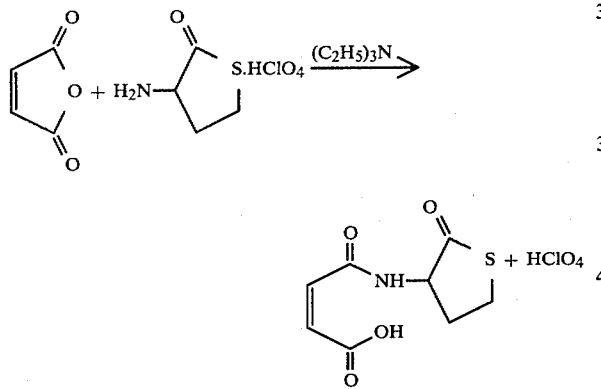

N-Maleamide homocysteine thiolactone amide is formed by reaction of homocysteine thiolactone hydroperchlorate with maleimide in a non-polar solvent, such as toluene, catalyzed by triethylamine:

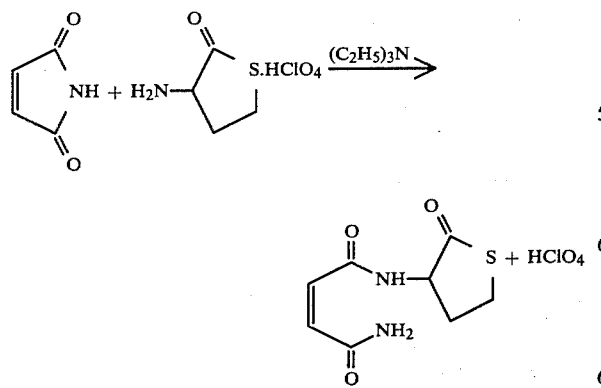

Oxalyl homocysteine thiolactone hydroperchlorate is formed by reaction of homocysteine thiolactone hydroperchlorate with oxalyl chloride in a non-polar solvent, such as tetrahydrofuran and methylene chloride:

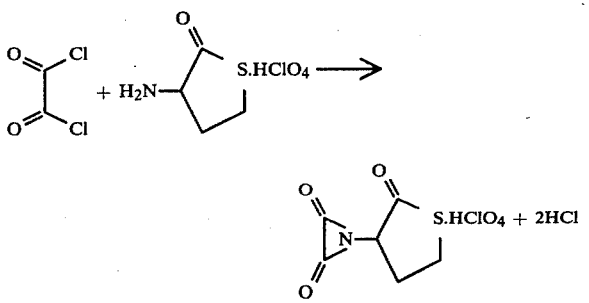

Attempted synthesis of this compound using homocysteine thiolactone free base failed, owing to undesirable side reactions though to include dimerization and polymerization.

The solid rhodium complex is formed by reaction of rhodium trichloride with oxalyl homocysteine thiolactone hydroperchlorate in methanolic solution:

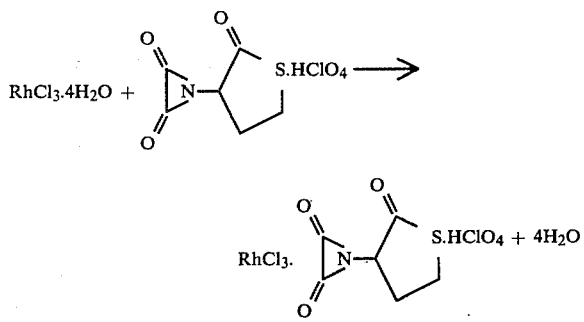

N-Maleyl and N-maleamide homocysteine thiolactone amides have anti-neoplastic activity, demonstrated by results of tests on mice having transplanted A-10 ascites mammary carcinoma. These compounds are not toxic.

Rhodium carboxylates are reported to have anti-neoplastic, chemotherapeutic activity in experimental animals, *Proc. Soc. Exp. Biol. Med.*, 145:1278–1283 (1974), but these complexes have appreciable toxicity. A review of transition metal complexes in cancer chemotherapy is given in *Coord. Chem. Rev.*, 12:349–405 (1974).

Rhodium salts also have anti-viral activity in animals, *Brit. J. Exper. Path.*, 39:480–489 (1958) and prolong the life span of rats, *J. Nutr.*, 101:1431–1438 (1971).

Neither oxalyl homocysteine thiolactone nor the rhodium complex of oxalyl homocysteine thiolactone is toxic to mice at a level of 50 mg/kg/day. The rhodium complex of oxalyl homocysteine thiolactone provides a non-toxic, stable form of rhodium, which is soluble in some organic solvents and stable in aqueous buffer at pH 7.4 for administration to animals. It is expected that oxalyl homocysteine thiolactone and the rhodium complex of oxalyl homocysteine thiolactone will also have anti-neoplastic, chemotherapeutic activity in animals.

The physiochemical properties of several of the derivatives of homocysteine thiolactone are unexpected for sulfur amino acids. Previously known derivatives of homocysteine, homocysteine, and homocysteine thiolactone are colorless; i.e., their solutions fail to absorb visible light. Solutions of compounds of this invention, N-maleamide homocysteine thiolactone amide, oxalyl homocysteine thiolactone hydroperchlorate, and rhodium trichloride oxalyl homocysteine thiolactone hydroperchlorate all absorb visible light to a greater or lesser extent.

N-Maleamide homocysteine thiolactone amide is yellow and forms intensely yellow solutions in various solvents. Oxalyl homocysteine thiolactone is a black oil, which dissolves in organic solvents to form an intensely brown-black solution. This material absorbs sunlight almost completely. Since it is stable to heating, oxidation, and chemical degradation, it is useful for capturing solar energy, either in the form of heat or, because of its electrophilic properties, for photovoltaic generation of electricity. Oxalyl homocysteine thiolactone, dissolved in methanol, forms complexes with metal ions, especially Cu, Ni, Mn, Fe, Co, Mg, Hg, Ca, Cr, Ba, Zn, Pt, and Rh. Oxalyl homocysteine thiolactone and these metal complexes with oxalyl homocysteine thiolactone are decomposed by contact with water. However, the rhodium complex of oxalyl homocysteine thiolactone forms a stable red-brown solution in aqueous buffer (pH 7.4). In the presence of visible light this solution slowly evolves gas, which shows that light energy is captured and coupled to the decomposition of water, yielding oxygen and hydrogen.

Due to their anti-neoplastic activity, the compounds of this invention are useful as anti-neoplastic agents in human and veterinary medicine. These compounds are effective against A-10 ascites mammary carcinoma. In addition to their use in vitro, they can be employed, for example, in the parenteral therapy of neoplasms.

The compounds of this invention can be employed in mixture with conventional excipients, i.e., pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and, if desired, mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

The compounds of this invention are generally administered to animals, including but not limited to mammals, e.g., household pets, humans, cattle, cats and dogs.

Parenteral administration is preferred, the compounds of this invention being particularly valuable in the treatment of mammals afflicted with malignant neoplasms. Intraperitoneal administration is most preferred.

It will be appreciated that the actual preferred amounts of active compounds used will vary according to the specific compound being utilized, the particular compositions formulated, the mode of application, and the particular situs and organism being treated. Optimal application rates for a given set of conditions can be ascertained by those skilled in the art using conventional dosage determination tests in view of the above guidelines.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following examples, the temperatures are set forth uncorrected in degrees Celsius. Unless otherwise indicated, all parts and percentages are by weight.

EXAMPLE 1

Preparation of Homocysteine Thiolactone Perchlorate

Homocysteine thiolactone perchlorate was prepared by suspending 30 g of homocysteine thiolactone hydrochloride (Nutritional Biochemicals) in 1000 ml of chloroform-methanol (4:1, by volume). Two equivalents of 70% $HClO_4$ were added dropwise with stirring until solution was achieved. The solution was concentrated on a rotary evaporator to crystallize the homocysteine thiolactone perchlorate. The crystals were recrystallized to give translucent, white crystals with a sharp melting point at 186° C., light-absorption maximum in water 238 nm (found: C, 22.2; H, 3.3; Cl, 16.4; N, 6.6; O, 36.8; S, 14.9; $C_4H_8ClNO_5S$ requires C, 22.1; H, 3.7; Cl, 16.3; N, 6.4; O, 36.8; S, 14.7%). The crystals yielded a single ninhydrin positive spot, $R_f$0.58, on Mallinckrodt silica gel TLC-TGF plates in chloroform-methanol (4:1, by volume) and a single uniform peak in the position expected for homocysteine thiolactone on the Beckman 120C Amino Acid Analyzer.

EXAMPLE 2

Preparation of N-Maleyl Homocysteine Thiolactone Amide

Maleic anhydride (4.9 g) was dissolved in 75 ml of toluene at 24° C. Then 10.9 g of homocysteine thiolactone hydroperchlorate was suspended in the solution. To the resulting stirred mixture was gradually added 5.0 g of triethylamine. The mixture was stirred until a solution was obtained. After 30 minutes' further stirring, a white solid precipitated out. Toluene was decanted from the solid, which was triturated in 75 ml of 0.2 M HCl, rinsed with dilute HCl, and dried in vacuo. The white powder was crystallized from acetonitrile to yield 7.3 g of N-maleyl homocysteine thiolactone amide (68% of theoretical). MP 153°–153.5° C.

Analysis: C, 44.5; H, 4.42; N, 6.65; S, 14.5; ($C_8H_9O_4NS$).

EXAMPLE 3

Preparation of N-Maleamide Homocysteine Thiolactone Amide

In a solution of 3.9 g of maleimide in 200 ml toluene was suspended 8.7 g of homocysteine thiolactone hydroperchlorate. To the resulting mixture was added 4.0 g of triethylamine with stirring. This mixture was heated under reflux for one hour and cooled. Toluene was removed using a rotary evaporator to give a solid residue, which was thoroughly mixed and extracted with 100 ml of cold ethyl ether in several portions. The resulting viscous orange residue was dissolved in 400 ml of hot 95% ethanol, filtered, and cooled. The yellow precipitate was recrystallized from 95% ethanol to yield 4.7 g of N-maleamide homocysteine thiolactone amide (55% of theoretical). MP 80°-82° C.

Analysis: C, 44.9; H, 4.95; N, 13.0; S, 14.4, ($C_8H_{10}O_3N_2S$).

EXAMPLE 4

Preparation of Oxalyl Homocysteine Thiolactone Hydropechlorate

To a stirred solution of 3.7 g of homocysteine thiolactone hydroperchlorate in 100 ml of tetrahydrofuran:methylene chloride (1:1 by volume) was added 7.6 g of oxalyl chloride. The resulting mixture was kept at 37° for 18 hours. The solvent was evaporated under reduced pressure and the resulting black residue was dissolved in 50 ml of methylene chloride. The solution was filtered and the solvent evaporated from the filtrate under reduced pressure. The residue was extracted repeatedly with petroleum ether until the ether layer was clear. After drying, the black viscous oil weighed 4.6 g (98% of theoretical). Oxalyl homocysteine thiolactone hydroperchlorate is shown by NMR 60 MHz (singlet 8.2, multiplets 4.3, 3.5, and 1.7 ppm).

This substance is soluble in dimethyl sulfoxide, methanol, methylene chloride, ethanol, tetrahydrofuran, and acetonitrile.

Oxalyl homocysteine thiolactone hydroperchlorate is highly colored and dissolves in polar and non-polar solvents to form intensely dark brown-black clear solutions. The substance decomposes on contact with water to form a white, gummy precipitate. The substance is a viscous, brown-black oil with a fruity, vitamin-like odor. Solidification or precipitation does not occur when the substance is cooled.

EXAMPLE 5

Preparation of Rhodium Trichloride Homocysteine Thiolactone Hydroperchlorate Complex To a solution of 1.0 g of rhodium trichloride. 4 $H_2O$ in 180 ml of methanol was added a solution of 1.0 g of oxalyl homocysteine thiolactone hydroperchlorate in 100 ml of methanol slowly with mixing at 22°. After 90 minutes' stirring, the solution was filtered and the slight brown precipitate was discarded. The solvent was evaporated under reduced pressure and the viscous orange residue was dried in vacuo. The residue was extracted with 300 ml of ethyl acetate in 50 ml portions, filtered, and dried to yield 0.57 g of red powder. The rhodium trichloride oxalyl homocysteine thiolactone hydroperchlorate complex is shown by NMR 60 MHz (broad peaks, 1.8, 3.5, 3.8, 4.4 ppm).

The complex is highly soluble in dimethyl sulfoxide, methanol and ethanol and slightly soluble in tetrahydrofuran and acetonitrile, in which clear intensely red-brown solutions were obtained.

EXAMPLE 6

Evaluation of Homocysteine Thiolactone Perchlorate on Influencing the Growth of a Malignant Neoplasm in Mice The protocol utilized was daily doses of homocysteine thiolactone perchlorate ($HCT.HClO_4$) 2.5 mg/kg/day for 10 days. It was found that the amount of necrosis in the transplanted murine mammary adenocarcinoma increased. $1.5-2.0 \times 10^7$ A-10 ascites cells were injected subcutaneously in 6 week-old female A/HeJ mice obtained from Jackson Labs, Bar Harbor. Maine. After two weeks the tumors were dissected, weighed, bisected, and reweighed. During the final ten days of tumor growth, homocysteine thiolactone perchlorate, 2.5 mg/kg/day, was injected intraperitoneally. In the chart below are the tumor weights, before and after washing, as well as the difference in weight which is proportional to the amount of necrosis in the tumor.

The values in the chart below were calculated for differences between control and experimental groups, using the paired T test. This experiment showed that homocysteine thiolactone perchlorate affected the growth of a malignant neoplasm by causing increased necrosis within the tumor.

| Compound | No. of Tumors | Mean Weight (g + SEM) Before Washing | P | After Washing | P | Difference | P |
|---|---|---|---|---|---|---|---|
| — | 7 | 2.383 ± 0.154 | — | 2.111 ± 0.136 | — | .231 ± 0.037 | — |
| $HCT.HClO_4$ | 7 | 2.507 ± 0.100 | 0.1 | 2.197 ± 0.099 | 0.1 | .326 ± 0.029 | .06 |

EXAMPLE 7

Evaluation of N-Maleyl Homocysteine Thiolactone Amide and N-Maleamide Homocysteine Thiolactone Amide on Influencing Growth of a Malignant Neoplasm in Mice Daily dose of the N-maleyl compound (I) and the N-maleamide compound (II) of 10 mg/kg/day were injected intraperitoneally for eleven days following transplantation of A-10 ascites mammary carcinoma cells in a subcutaneous site in A/HeJ mice obtained from Jackson Labs, Bar Harbor, Maine. The subcutaneous neoplasms were dissected and weighed as described in Example 6. Results were:

| Compound | Number | Weight (g + SEM) | P |
|---|---|---|---|
| — | 19 | 0.60 ± 0.034 | — |
| I | 23 | 0.44 ± 0.038 | <0.01 |
| II | 25 | 0.50 ± 0.038 | <0.05 |

The P values were calculated for differences between control and experimental groups, using the paired T test. The data show that I and II decrease the growth of a malignant neoplasm in mice.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

EXAMPLE 8

Toxicity Testing

A/HeJ female mice were injected with A-10 tumor cells, as described in Example 6. A/J female mice were injected with AK 15091 tumor fragments using the procedure in Example 6. In both cases the compound was administered intraperitoneally for 10 days. In the chart below are the number and condition of the survivors for each group. These tests showed that these compounds are not toxic at the doses indicated because there was no significant difference in survival and condition of the mice injected with vehicle, oxalyl homocysteine thiolactone, or rhodium trichloride oxalyl homocysteine thiolactone. The few deaths observed are at a rate similar to that found in DMSO alone in many similar experiments, although no deaths were reported for DMSO in this particular experiment.

| Compound | Dose | Tumor | Strain | Condition | Survivors |
|---|---|---|---|---|---|
| Oxalyl homocysteine thiolactone | 50 mg/kg | AK15091 | A/J | Good | 16/16 |
| Rhodium trichloride oxalyl homocysteine thiolactone | 5 | AK15091 | A/J | Good | 16/16 |
| Same | 50 | AK15091 | A/J | Good | 16/17 |
| Same | 5 | A-10 | A/HeJ | Good | 27/28 |
| Same | 50 | A-10 | A/HeJ | Good | 26/28 |
| None, DMSO vehicle | — | AK15091 | A/J | Good | 25/25 |

I claim:

1. A compound of the formula

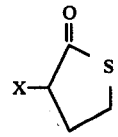

wherein X is cis—HOCOCH=CHCONH—, cis—H$_2$NCOCH=CHCONH—,

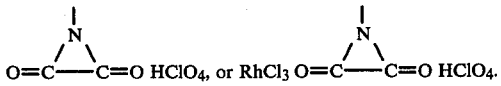

O=C——C=O HClO$_4$, or RhCl$_3$ O=C——C=O HClO$_4$.

2. N-Maleyl homocysteine thiolactone amide, a compound of claim 1.

3. N-Maleamide homocysteine thiolactone amide, a compound of claim 1.

4. Oxalyl homocysteine thiolactone hydroperchlorate, a compound of claim 1.

5. Rhodium trichloride oxalyl homocysteine thiolactone hydroperchlorate, a compound of claim 1.

6. A method of decreasing the growth of a malignant neoplasm comprising administering to an animal afflicted with the neoplasm a compound of claim 1, in admixture with a pharmaceutically acceptable carrier, in an amount effective to decrease the growth of the neoplasm.

7. A method of decreasing the growth of a malignant neoplasm comprising administering to an animal afflicted with the neoplasm a compound of claim 2, in admixture with a pharmaceutically acceptable carrier, in an amount effective to decrease the growth of the neoplasm.

8. A method of decreasing the growth of a malignant neoplasm comprising administering to an animal afflicted with the neoplasm a compound of claim 3, in admixture with a pharmaceutically acceptable carrier, in an amount effective to decrease the growth of the neoplasm.

9. A method of decreasing the growth of a malignant neoplasm comprising administering intraperitoneally to an animal afflicted with the neoplasm a compound of claim 1, in admixture with a pharmaceutically acceptable carrier, in an amount effective to decrease the growth of the neoplasm.

* * * * *